(12) United States Patent
Li et al.

(10) Patent No.: US 11,959,933 B2
(45) Date of Patent: Apr. 16, 2024

(54) EXPERIMENTAL DEVICE AND METHOD FOR SUPERCRITICAL CO2/H2O MIXED FLUID HUFF AND PUFF FOR SHALE OIL DEVELOPMENT

(71) Applicant: CHINA UNIVERSITY OF PETROLEUM (EAST CHINA), Qingdao (CN)

(72) Inventors: Lei Li, Qingdao (CN); Yuliang Su, Qingdao (CN); Yongmao Hao, Qingdao (CN); Wendong Wang, Qingdao (CN); Xiaomei Zhou, Qingdao (CN); Xue Zhang, Qingdao (CN); Zheng Chen, Qingdao (CN)

(73) Assignee: CHINA UNIVERSITY OF PETROLEUM (EAST CHINA), Qingdao (CN)

( * ) Notice: Subject to any disclaimer, the term of this patent is extended or adjusted under 35 U.S.C. 154(b) by 176 days.

(21) Appl. No.: 17/804,136

(22) Filed: May 26, 2022

(65) Prior Publication Data

US 2022/0390342 A1    Dec. 8, 2022

(51) Int. Cl.
*G01N 5/02* (2006.01)
*G01N 1/38* (2006.01)
(Continued)

(52) U.S. Cl.
CPC ............... *G01N 5/02* (2013.01); *G01N 1/38* (2013.01); *G01N 24/081* (2013.01); *G01N 33/241* (2013.01)

(58) Field of Classification Search
CPC ...... G01N 1/38; G01N 24/081; G01N 33/241; G01N 5/02
See application file for complete search history.

(56) References Cited

U.S. PATENT DOCUMENTS

2013/0144533 A1*  6/2013  Kim .................... G01N 15/0806
                                                    702/12
2019/0025169 A1*  1/2019  Zhang ...................... G01N 3/04

FOREIGN PATENT DOCUMENTS

CN     105784567 A  *  7/2016  ......... G01N 15/0826
CN     108362614 A  *  8/2018  ............. G01N 13/04
(Continued)

OTHER PUBLICATIONS

Li Erdang; Study on microscopic pore utilization characteristics of displacement dense reservoirs with different gas injection media full text 1-5 Petroleum Drilling Technology , forty-eighth vol. 5 Full text Publication date: Sep. 30, 2020.
(Continued)

*Primary Examiner* — Natalie Huls
(74) *Attorney, Agent, or Firm* — CBM PATENT CONSULTING, LLC

(57) ABSTRACT

An experimental device and method for supercritical $CO_2$/$H_2O$ mixed fluid huff and puff for shale oil development includes a $CO_2$ storage tank, a water vapor generator, a mixing vessel, and a core holder; the $CO_2$ storage tank and the water vapor generator are in communication with the mixing vessel; a first pressure gauge and a hygronom are connected to an upper end of the mixing vessel, and a displacement pump is connected to a lower end of the mixing vessel; the mixing vessel is connected to an inlet end of the core holder; the core holder is connected to an inlet end of a drying pipe, and the measuring cylinder is disposed upside down in a liquid containing dish, where the liquid containing dish and the measuring cylinder are filled with a saturated sodium carbonate solution.

5 Claims, 4 Drawing Sheets

(51) Int. Cl.
G01N 24/08 (2006.01)
G01N 33/24 (2006.01)

(56) References Cited

FOREIGN PATENT DOCUMENTS

| CN | 108414385 A | * | 8/2018 | ............... G01N 5/00 |
| CN | 111238988 A | * | 6/2020 | ............... G01N 5/02 |
| CN | 111257540 A | * | 6/2020 | ............. G01N 33/24 |
| CN | 112664176 A | * | 4/2021 | |

OTHER PUBLICATIONS

Babak Iraji, Experimental nvestigation of CO2 huff and puff in a matrix-fracture system Fuel vol. 158, pp. 105-112 Publication date: Oct. 15, 2015.

* cited by examiner

EXPERIMENTAL DEVICE AND METHOD FOR SUPERCRITICAL CO2/H2O MIXED FLUID HUFF AND PUFF FOR SHALE OIL DEVELOPMENT

CROSS REFERENCES

This application claims priority to Chinese Patent Application Ser. No. CN2021105903442 filed on 828 May 2021.

FIELD OF THE INVENTION

The present disclosure relates to the field of petroleum engineering—oil and gas field development engineering, particularly to unconventional reservoir development, and more particularly to an experimental device and method for supercritical $CO_2/H_2O$ mixed fluid huff and puff for shale oil development.

BACKGROUND OF THE INVENTION

With the exploration and development of oil and gas resources, the demands for oil and natural gas are increasing, which causes a decrease in the reserves of the conventional oil and gas resources, and makes the unconventional oil and gas resources (tight oil, shale gas, shale oil, etc.) become more and more important in the oil industry. China has huge shale oil reserves, with the geological reserves all over the county of up to $1420*10^8$ t, in which the recoverable reserves reach $30*10^8$ t to $60*10^8$ t, providing good prospects in development. At present, the comprehensive application of horizontal well and multistage fracturing technologies has become an effective way for developing shale reservoirs. However, depletion development of shale oil often has low single well production, rapid production declination, and low recovery efficiency (5% to 10%). Due to the extremely low permeability and porosity of shale reservoirs, and the existence of abundant brittle clay minerals in reservoir rocks, the conventional water flooding secondary development will cause the expansion of shale, thus being difficult to be used for shale reservoirs. Gas injection development has the advantages of effectively improving the physical properties of reservoirs, reducing the viscosity of crude oil in the reservoirs, and expanding the volume of crude oil. Compared with water flooding development, gas injection development will become an effective measure for developing shale reservoirs.

Gas injection development is a commonly used secondary oil recovery technology. Gas injection could be in a gas flooding mode or in a huff and puff mode, and also could be miscible or immiscible according to the pressure. Huff and puff gas injection uses one well as both the injection well and the production well, thereby solving the problem of gas channeling in the shale oil reservoir after fracturing by conventional gas flooding. Regarding the injection medium, supercritical $CO_2$, as the most widely used gas flooding agent, has the potential to efficiently develop shale oil. Compared with $CH_4$ and $N_2$, supercritical $CO_2$ is more likely to be miscible with crude oil, so that the flow capacity of oil is improved, and the recovery efficiency is increased by 5%-25% from the original. However, its gas viscosity is low, resulting in a low sweep efficiency. $CO_2$ water-gas alternate flooding combines the advantages of $CO_2$ flooding and water flooding, which can increase the sweep efficiency and greatly improve the oil recovery. However, in the process of $CO_2$ water-gas alternate injection into shale reservoirs, the problems of decreased injection capacity and increased injection pressure are present, which impacts the development effect of water-gas alternate injection. On this basis, a supercritical $CO_2/H_2O$ mixed fluid huff and puff method for improving shale oil recovery is designed. The method can give full play to the advantages of $CO_2$ huff and puff and water-gas alternate injection, so as to increase the viscosity of the injection medium, slow down gas channeling, improve the energy efficiency and sweep efficiency of the injection medium, and increase the oil production. There is no report on such research so far, and it is necessary to design experiments to assess the effect of this method in increasing the production.

SUMMARY OF THE INVENTION

An object of the present disclosure is to provide an experimental device and method for supercritical $CO_2/H_2O$ mixed fluid huff and puff for shale oil development, which allows the effect of huff and puff with different parameters to be assessed by experiments, and has great importance in practice for promoting the efficient development of shale oil.

The present disclosure adopts the following technical scheme:

an experimental device for supercritical $CO_2/H_2O$ mixed fluid huff and puff for shale oil development includes a $CO_2$ storage tank, a water vapor generator, a mixing vessel, and a core holder, where the $CO_2$ storage tank is in communication with the mixing vessel via a $CO_2$ delivery pipeline, and the $CO_2$ delivery pipeline is provided with a first booster pump; the water vapor generator is in communication with the mixing vessel via a water vapor delivery pipeline, and the water vapor delivery pipeline is provided with a second booster pump;

a first pressure gauge and a hygronom are connected to an upper end of the mixing vessel, a displacement pump is connected to a lower end of the mixing vessel, and the mixing vessel is connected to a vacuum pump; the mixing vessel is connected to an inlet end of the core holder via a mixed fluid delivery pipeline, and the mixed fluid delivery pipeline is provided with a gas flow meter, a third booster pump, an injection valve and a second pressure gauge in sequence;

the core holder is connected to a hand pump via a confining pressure application pipeline, and the confining pressure application pipeline is provided with a third pressure gauge; the inlet end of the core holder is connected to an inlet end of a drying pipe via an oil-gas extraction pipeline, the oil-gas extraction pipeline is provided with a two-way valve, degreasing cotton is provided inside the drying pipe, an outlet end of the drying pipe is connected to a measuring cylinder via a gas extraction pipeline, and the measuring cylinder is disposed upside down in a liquid containing dish, where the liquid containing dish and the measuring cylinder are filled with a saturated sodium carbonate solution; an outlet end of the core holder is provided with a fourth pressure gauge for observing outlet pressure in real time; and the mixing vessel, the first pressure gauge, the hygronom, the gas flow meter, the third booster pump, the injection valve, the second pressure gauge, the two-way valve, the core holder and the fourth pressure gauge are all arranged in a thermostat chamber.

An experimental method for supercritical $CO_2/H_2O$ mixed fluid huff and puff for shale oil development, using the experimental device described above, includes the following steps:

at step (1), measuring the dry weight, length, and diameter of a rock core, and saturating the rock core with a simulated oil; and measuring the wet weight of the rock core to calculate the amount of the saturated oil;

at step (2), carrying out a supercritical $CO_2/H_2O$ huff and puff experiment:

at i), preparing a supercritical $CO_2/H_2O$ mixed fluid of a certain ratio in the mixing vessel;

at a., establishing a relation formula by the following steps:

converting relative humidity into molar content of water vapor in gas according to the following formulas:

relative humidity:

$$\frac{e}{E} = \varphi \quad (1)$$

where:
e—actual water vapor pressure in humid air, Pa
E—saturated water vapor pressure at the same temperature, Pa
φ—relative humidity
conversion formulas:

$$\varphi = \frac{P \cdot h}{P_0} \quad (2)$$

$$h = \frac{\varphi \cdot P_0}{P} \quad (3)$$

$$\frac{h}{P_0} = \frac{\varphi}{P} \quad (4)$$

where:
φ—relative humidity
P—gas pressure in the vessel, Pa
h—molar content of water vapor in gas
$P_0$—saturated vapor pressure of water at experimental temperature at b., turning on the thermostat chamber to make the temperature in the thermostat chamber be constant; and turning on the vacuum pump to vacuumize the mixing vessel and the pipelines;

opening the $CO_2$ storage tank, injecting a certain amount of $CO_2$ gas into the mixing vessel via the first booster pump and the $CO_2$ delivery pipeline, and reading the pressure of the mixing vessel from the first pressure gauge; then, turning on the water vapor generator, introducing water vapor into the mixing vessel via the second booster pump and the water vapor delivery pipeline, and recording the pressure and relative humidity of the mixing vessel from the first pressure gauge and the hygronom, respectively;

with the formula (4), according to the molar content and temperature of water vapor in a mixed fluid designed in an experiment scheme, when the ratio of the relative humidity and the pressure meets requirements of the experiment, turning off the water vapor generator to complete the preparation of a mixed fluid with a certain content of water vapor; and then recording the pressure of the mixing vessel;

at ii), putting the oil-saturated rock core of step (1) into the core holder, and applying a confining pressure to the core holder by the hand pump, the confining pressure applied being displayed by the third pressure gauge;

opening the injection valve, injecting the prepared mixed fluid with a certain molar fraction of water vapor into the core holder by the third booster pump while keeping the pressure of the mixing vessel constant by the displacement pump, keeping the injection pressure, after reaching an experiment pressure, stable for a certain period of time, and recording the volume of injected gas from the gas flow meter; and at iii), shutting off the injection valve, carrying out shut-in on the core holder, and monitoring the pressure during shut-in in real time by the second pressure gauge and the fourth pressure gauge;

weighing the original weight of the degreasing cotton before putting the degreasing cotton into the drying pipe, opening the two-way valve when the shut-in is completed for flowback of liquid and gas, then weighing the weight of the degreasing cotton to measure the amount of produced oil, and measuring the amount of $CO_2$ flowed back by the measuring cylinder; and obtaining an oil recovery according to the ratio of the measured amount of produced oil to the amount of saturated oil as the measurement result of the experiment.

Preferably, the experimental method described above further includes the steps:

before the supercritical $CO_2/H_2O$ huff and puff experiment, putting the rock core saturated with the simulated oil into nuclear magnetic resonance equipment to test the distribution of the simulated oil in the rock core; and after the experiment is finished, putting the rock core into the nuclear magnetic resonance equipment to test the distribution of the simulated oil in the rock core.

Preferably, the experimental method described above further includes combining supercritical $CO_2/H_2O$ mixed fluid huff and puff with thermal oil recovery, and the method further includes the steps:

at the beginning of shut-in, in a stage where supercritical $CO_2/H_2O$ interacts with the rock core, adjusting the temperature of the thermostat chamber to 380-400° C. to reach the supercritical state of $H_2O$.

Preferably, the experimental method described above further includes a step of calculating the storage factor of supercritical $CO_2$:

after injecting $CO_2$ into the mixing vessel, reading the pressure of the mixing vessel from the first pressure gauge, and calculating the amount of $CO_2$ in the mixing vessel according to the ideal gas law;

the ideal gas law being as follows:

$$PV = nZRT \quad (5)$$

where:
P—pressure of gas, Pa
V—volume of gas, m³
n—amount of substance of gas, mol
Z—compressibility factor of gas;
R—proportionality coefficient, J/(mol·K)
T—system temperature, K converting the volume of $CO_2$ at atmospheric pressure measured by the measuring cylinder to a volume of $CO_2$ at the pressure of the mixing vessel:

first, deriving a compressibility factor of carbon dioxide at the pressure of the mixing vessel by the formula (5):

$$Z_1 = \frac{P_1 V_1}{n_1 R T_1} \tag{6}$$

where:

$P_1$—pressure of carbon dioxide at the pressure of the mixing vessel, Pa $V_1$—volume of carbon dioxide at the pressure of the mixing vessel, m³

$n_1$—amount of substance of carbon dioxide at the pressure of the mixing vessel, mol $Z_1$—compressibility factor of carbon dioxide at the pressure of the mixing vessel;

$T_1$—temperature at the pressure of the mixing vessel, K obtaining a compressibility factor of carbon dioxide with the equivalent amount of substance at atmospheric pressure:

$$Z_2 = \frac{P_2 V_2}{n_1 R T_2} \tag{7}$$

where:

$P_2$—atmospheric pressure, Pa $V_2$—volume of carbon dioxide at atmospheric pressure, m³

$n_1$—amount of substance of carbon dioxide at atmospheric pressure, mol $Z_2$—compressibility factor of carbon dioxide at atmospheric pressure;

$T_2$—room temperature, K converting the volume of carbon dioxide at atmospheric pressure into a volume at the pressure of the mixing vessel by the following formula:

$$V_1 = \frac{Z_1 P_2 V_2 T_1}{Z_2 P_1 T_2} \tag{8}$$

and calculating the storage factor of supercritical $CO_2$ by the following formula:

$$\eta = \frac{V_{flowback}}{V_{injection}} \tag{9}$$

where:

$\eta$—storage factor of supercritical $CO_2$;

$V_{injection}$—volume of actually injected mixed fluid, m³

$V_{flowback}$—volume at the pressure of the mixing vessel converted from the volume of $CO_2$ flowed back measured by the measuring cylinder, m³.

Preferably, in the method described above, during the flowback of liquid and gas after the shut-in is finished, the flowback pressure is successively decreased by 5 MPa until the pressure is reduced to the atmospheric pressure.

The present disclosure has the following beneficial effects:

According to the present disclosure, the actual huff and puff production process of shale reservoirs is simulated to design an experimental device and method for simulating the effect of supercritical $CO_2/H_2O$ mixed fluid huff and puff in improving the recovery of shale reservoirs, and the effect of huff and puff with different parameters can be assessed by experiments, thereby solving the problem in the prior art that there is a lack of experimental device and method for assessing the effect of supercritical $CO_2/H_2O$ mixed fluid huff and puff in improving the recovery of shale oil. In addition, the method and device heats the rock core after the injection of supercritical $CO_2/H_2O$ to simulate the in-situ reservoir heating technology, so that the effect of supercritical $CO_2/H_2O$ huff and puff and thermal oil recovery can be assessed, and the problem of large heat loss of conventional thermal recovery methods such as hot-fluid injection can be improved.

The device provided by the present disclosure is simple and easy to operate, and the method involves simple steps and provides accurate measurement in which the ratio of $CO_2$ and $H_2O$ can be controlled as needed, providing valuable reference for the research on supercritical $CO_2/H_2O$ mixed fluid huff and puff for shale oil development, and making up for the blank of the research on supercritical $CO_2/H_2O$ mixed fluid huff and puff for shale oil development.

BRIEF DESCRIPTION OF THE DRAWINGS

The present disclosure will now be further described with reference to the accompanying drawings and detailed description.

In FIG. 1, 1. $CO_2$ storage tank, 2. first booster pump, 3. second booster pump, 4. water vapor generator, 5. first pressure gauge, 6. hygronom, 7. mixing vessel, 8. vacuum pump, 9. gas flow meter, 10. third booster pump, 11. injection valve, 12. second pressure gauge, 13. two-way valve, 14. drying pipe, 15. degreasing cotton, 16. hand pump, 17. third pressure gauge, 18. core holder, 19. fourth pressure gauge, 20. measuring cylinder, 21. liquid containing dish, 22. thermostat chamber, and 23. displacement pump.

DETAILED DESCRIPTION OF THE EMBODIMENTS

Figure 1:
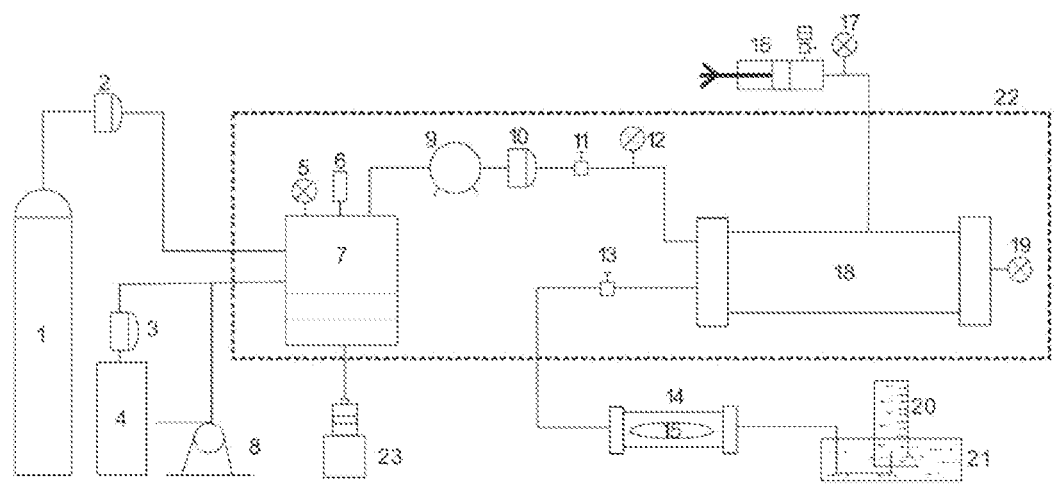
FIG. 1 shows a schematic diagram illustrating the structure and principle of an experimental device for supercritical $CO_2/H_2O$ mixed fluid huff and puff for shale oil development according to the present disclosure.

The inventors of the present application have found that the method of developing shale oil by supercritical $CO_2/H_2O$ mixed fluid huff and puff can give plays to the advantages of both fluids. In the process of supercritical $CO_2/H_2O$ mixed fluid huff and puff, $CO_2$ dissolved in water can cause water to become weakly acidic, and the acidity of water can be increased especially at high temperature, which provides chemical conditions to change the properties of rock. Under the acid condition, unstable minerals will undergo acid-induced reactions to change the composition of the minerals, and the contents of carbonate (calcite and dolomite) and feldspar (albite and potash feldspar) will decrease to varying degrees. Due to the weak solubility of quartz and clay in acid, the composition of chlorite, illite and kaolinite will also change to varying degrees. The dissolution of carbonate, feldspar, chlorite and quartz to varying degrees forms dissolution pores, thereby improving the porosity and permeability of the reservoir and improving the effect of development. The water in the mixed fluid increases the density of the injection fluid, reduces the mobility ratio between the injection fluid and the crude oil, and prevents the occurrence of rapid channeling of $CO_2$, thereby achieving a more balanced development, increasing the sweep efficiency, and achieving a better oil displacement effect. After the injection of supercritical $CO_2/H_2O$, the reservoir is heated to the supercritical state of $H_2O$, and the high solubility, high diffusivity and high reactivity of supercritical water can improve the sweep efficiency and oil displacement efficiency during oil displacement, so that the recovery is improved. In addition, the injection of the displacement medium followed by heating solves the problem of large heat loss of conventional thermal recovery methods such as heat-fluid injection. Therefore, the technology of improving the recovery of shale oil by supercritical $CO_2/H_2O$ mixed fluid huff and puff is a very promising new technology for shale oil development, which has great importance in practice for promoting the efficient development of shale oil.

On this basis, the present disclosure provides an experimental device and method for supercritical $CO_2/H_2O$ mixed fluid huff and puff for shale oil development, which simulates the actual huff and puff process of shale oil development so assess the effect of huff and puff with different parameters by experiments, thereby solving the problem in the prior art that there is a lack of experimental method for assessing the effect of supercritical $CO_2/H_2O$ mixed fluid huff and puff in improving the recovery of shale oil. In addition, the device and method heats the rock core to 380-400° C. after the injection of supercritical $CO_2/H_2O$ to reach the supercritical state of $H_2O$, and this combines the supercritical $CO_2/H_2O$ mixed fluid huff and puff with thermal oil recovery, providing valuable reference for the research on supercritical $CO_2/H_2O$ mixed fluid huff and puff for shale oil development, and making up for the blank of the research on supercritical $CO_2/H_2O$ mixed fluid huff and puff for shale oil development.

As shown in FIG. 1, an experimental device for supercritical $CO_2/H_2O$ mixed fluid huff and puff for shale oil development includes a $CO_2$ storage tank 1, a water vapor generator 4, a mixing vessel 7 and a core holder 18. The $CO_2$ storage tank 1 is in communication with the mixing vessel via a $CO_2$ delivery pipeline, and the $CO_2$ delivery pipeline is provided with a first booster pump 2. The water vapor generator 4 in communication with the mixing vessel 7 via a water vapor delivery pipeline, and the water vapor delivery pipeline is provided with a second booster pump 3. A first pressure gauge 5 and a hygronom 6 are connected to an upper end of the mixing vessel 7, a displacement pump 23 is connected to a lower end of the mixing vessel, and the mixing vessel is connected to a vacuum pump 8. The mixing vessel 7 is connected to an inlet end of the core holder 18 via a mixed fluid delivery pipeline, and the mixed fluid delivery pipeline is provided with a gas flow meter 9, a third booster pump 10, an injection valve 11 and a second pressure gauge 12 in sequence.

The core holder 18 is connected to the hand pump 16 via a confining pressure application pipeline, and the confining pressure application pipeline is provided with a third pressure gauge 17. The inlet end of the core holder 18 is connected to an inlet end of a drying pipe 14 via an oil-gas extraction pipeline, the oil-gas extraction pipeline is provided with a two-way valve 13, and degreasing cotton 15 is provided inside the drying pipe 14. An outlet end of the drying pipe 14 is connected to a measuring cylinder 20 via a gas extraction pipeline, and the measuring cylinder 20 is disposed upside down in a liquid containing dish 21, where the liquid containing dish 21 and the measuring cylinder 20 are filled with a saturated sodium carbonate solution. An outlet end of the core holder 18 is provided with a fourth pressure gauge 19 for observing outlet pressure in real time. The mixing vessel 7, the first pressure gauge 5, the hygronom 6, the gas flow meter 9, the third booster pump 10, the injection valve 11, the second pressure gauge 12, the two-way valve 13, the core holder 18 and the fourth pressure gauge 19 are all arranged in a thermostat chamber 22.

The present disclosure also provides an experimental method for supercritical $CO_2/H_2O$ mixed fluid huff and puff for shale oil development, using the experimental device described above. The method specifically includes the following steps:

At step (1), the dry weight, length, and diameter of a rock core are measured, and the rock core is saturated with a simulated oil; and then the wet weight of the rock core is measured to calculate the amount of the saturated oil.

At step (2), the rock core saturated with the simulated oil is put into the nuclear magnetic resonance equipment to test the distribution of the simulated oil in the rock core.

At step (3), a supercritical $CO_2/H_2O$ huff and puff experiment is carried out.

At i), a supercritical $CO_2/H_2O$ mixed fluid of a certain ratio is prepared in the mixing vessel 7.

At a., a relation formula is established by the following steps:

Relative humidity is converted into molar content of water vapor in gas according to the following formulas:
Relative humidity:

$$\frac{e}{E} = \varphi \quad (1)$$

where:
e—actual water vapor pressure in humid air, Pa
E—saturated water vapor pressure at the same temperature, Pa
$\varphi$—relative humidity
Conversion formulas:

$$\varphi = \frac{P \cdot h}{P_0} \quad (2)$$

$$h = \frac{\varphi \cdot P_0}{P} \quad (3)$$

$$\frac{h}{P_0} = \frac{\varphi}{P} \quad (4)$$

where:
$\varphi$—relative humidity
P—gas pressure in the vessel, Pa
h—molar content of water vapor in gas
$P_0$—saturated vapor pressure of water at experimental temperature At b., the thermostat chamber 22 is turned on to make the temperature in the thermostat chamber be constant; and the vacuum pump 8 is turned on to vacuumize the mixing vessel 7 and the pipelines.

The $CO_2$ storage tank 1 is opened, a certain amount of $CO_2$ gas is injected into the mixing vessel 7 via the first booster pump 2 and the $CO_2$ delivery pipeline, and the pressure of the mixing vessel is read from the first pressure gauge 5. Then, the water vapor generator 4 is turned on, water vapor is introduced into the mixing vessel via the second booster pump 3 and the water vapor delivery pipeline, and the pressure and relative humidity of the mixing vessel are recorded from the first pressure gauge 5 and the hygronom 6, respectively.

With the formula (4), according to the molar content and temperature of water vapor in a mixed fluid designed in an experiment scheme, when the ratio of the relative humidity and the pressure meets requirements of the experiment, the water vapor generator is turned off to complete the preparation of a mixed fluid with a certain content of water vapor. Then the pressure of the mixing vessel is recorded.

At ii), the oil-saturated rock core of step (1) is put into the core holder, and a confining pressure is applied to the core holder by the hand pump 16, the confining pressure applied being displayed by the third pressure gauge 17.

The injection valve 11 is opened, the prepared mixed fluid with a certain molar fraction of water vapor is injected into the core holder 18 by the third booster pump 10, and the pressure of the third booster pump is controlled to obtain the supercritical state of carbon dioxide. The pressure of the mixing vessel 7 is then kept constant by the displacement pump 23, and the injection pressure, after reaching an experiment pressure, is kept stable for a certain period of time, and the volume of injected gas is recorded from the gas flow meter 9.

At iii), the injection valve is shut off, and shut-in is carried out on the core holder. At the beginning of shut-in, in a stage where supercritical $CO_2/H_2O$ interacts with the rock core, the temperature of the thermostat chamber is adjusted to reach the supercritical state of $H_2O$. The pressure is monitored during shut-in in real time by the second pressure gauge 12 and the fourth pressure gauge 19.

The initial weight of the degreasing cotton 15 is weighed before the degreasing cotton is put into the drying pipe 14, the two-way valve 13 is opened when the shut-in is completed for flowback of liquid and gas, and the flowback pressure is successively decreased by 5 MPa until the pressure is reduced to the atmospheric pressure. The weight of the degreasing cotton is weighed to measure the amount of produced oil, and the amount of $CO_2$ is flowed back by the measuring cylinder.

An oil recovery is obtained according to the ratio of the measured amount of produced oil to the amount of saturated oil as the measurement result of the experiment.

At step (4), after the experiment is finished, the rock core is put into the nuclear magnetic resonance equipment to test the distribution of the simulated oil in the rock core.

Furthermore, the method of the invention includes a step in which the storage factor of supercritical $CO_2$ is calculated:

After $CO_2$ is injected into the mixing vessel, the pressure of the mixing vessel 7 is read from the first pressure gauge, and the amount of $CO_2$ in the mixing vessel is calculated according to the ideal gas law.

The ideal gas law is as follows:

$$PV = nZRT \quad (5)$$

where:
P—pressure of gas, Pa
V—volume of gas, $m^3$
n—amount of substance of gas, mol
Z—compressibility factor of gas;
R—proportionality coefficient, J/(mol·K)
T—system temperature, K The volume of $CO_2$ at atmospheric pressure measured by the measuring cylinder is converted to a volume of $CO_2$ at the pressure of the mixing vessel:

Firstly, a compressibility factor of carbon dioxide at the pressure of the mixing vessel is derived by the formula (5):

$$Z_1 = \frac{P_1 V_1}{n_1 R T_1} \quad (6)$$

where:
$P_1$—pressure of carbon dioxide at the pressure of the mixing vessel, Pa
$V_1$—volume of carbon dioxide at the pressure of the mixing vessel, $m^3$
$n_1$—amount of substance of carbon dioxide at the pressure of the mixing vessel, mol
$Z_1$—compressibility factor of carbon dioxide at the pressure of the mixing vessel;
$T_1$—temperature at the pressure of the mixing vessel, K A compressibility factor of carbon dioxide with the equivalent amount of substance at atmospheric pressure is obtained as follows:

$$Z_2 = \frac{P_2 V_2}{n_1 R T_2} \quad (7)$$

where:
$P_2$—atmospheric pressure, Pa
$V_2$—volume of carbon dioxide at atmospheric pressure, $m^3$
$n_1$—amount of substance of carbon dioxide at atmospheric pressure, mol
$Z_2$—compressibility factor of carbon dioxide at atmospheric pressure;
$T_2$—room temperature, K Therefore, the volume of carbon dioxide at atmospheric pressure is converted into a volume at the pressure of the mixing vessel by the following formula:

$$V_1 = \frac{Z_1 P_2 V_2 T_1}{Z_2 P_1 T_2} \quad (8)$$

The storage factor of supercritical $CO_2$ is calculated by the following formula:

$$\eta = \frac{V_{flowback}}{V_{injection}} \quad (9)$$

where:
$\eta$—storage factor of supercritical $CO_2$;
$V_{injection}$—volume of actually injected mixed fluid, $m^3$
$V_{flowback}$—volume at the pressure of the mixing vessel converted from the volume of $CO_2$ flowed back measured by the measuring cylinder, $m^3$.

According to the experimental device and method of the present disclosure, with different molar contents of water vapor in mixed fluid and other conditions changed, the corresponding changes in the oil recovery and the storage factor of supercritical $CO_2$ can be obtained, thereby allowing the effect of huff and puff with different experimental conditions and parameters to be assessed by experiments, and making up for the blank of the research on supercritical $CO_2/H_2O$ mixed fluid huff and puff for shale oil development.

The present disclosure will be further illustrated by the following specific embodiments.

Embodiment 1

An experimental device for supercritical $CO_2/H_2O$ mixed fluid huff and puff for shale oil development is provided. The device includes a $CO_2$ storage tank 1, a first booster pump 2, a second booster pump 3, a water vapor generator 4, a first pressure gauge 5, a hygronom 6, a mixing vessel 7, a vacuum pump 8, a gas flow meter 9, a third booster pump 10, an injection valve 11, a second pressure gauge 12, a two-way valve 13, a drying pipe 14, degreasing cotton 15, a hand pump 16, a third pressure gauge 17, a core holder 18, a fourth pressure gauge 19, a measuring cylinder 20, a liquid containing dish 21, a thermostat chamber 22 and a displacement pump 23.

In use, firstly, the thermostat chamber 22 is turned on to make the temperature in the thermostat chamber 22 be constant. The vacuum pump 8 is turned on to vacuumize the mixing vessel 7 and the pipelines. The $CO_2$ storage tank 1 is opened, $CO_2$ is injected into the mixing vessel 7 by the first booster pump 2, and the pressure of the vessel is read from the first pressure gauge 5. The water vapor generator 4 is turned on, and water vapor is injected into the mixing vessel 7 by the second booster pump 3. The pressure is read from the first pressure gauge 5, and the relative humidity is read from the hygronom 6. When the ratio of the relative humidity and the pressure of vessel meets requirements of the experiment, the water vapor generator 4 is turned off. Then the pressure of the mixing vessel is recorded. An oil-saturated rock core is put into the core holder 18, and a confining pressure is applied to the core holder 18 by the hand pump 16, the confining pressure applied being displayed by the third pressure gauge 17. The injection valve 11 is opened, and a prepared mixed fluid with a certain molar fraction of water vapor is injected into the core holder 18 by the third booster pump 10 while the pressure in the mixing vessel 7 is kept constant by the displacement pump 23. The injection pressure, after reaching an experiment pressure, is kept stable for a certain period of time, and the volume of injected gas is recorded from the gas flow meter 9. The injection valve 11 is shut off, and shut-in is carried out on the core holder 18. At the beginning of shut-in, in a stage where supercritical $CO_2/H_2O$ interacts with the rock core, the temperature of the thermostat chamber is adjusted to reach the supercritical state of $H_2O$. The pressure is monitored during shut-in in real time by the second pressure gauge 12 and the fourth pressure gauge 19. The initial weight of the degreasing cotton 15 is weighed before the degreasing cotton is put into the drying pipe 14 The two-way valve 13 is opened when the shut-in is completed. The pressure is successively decreased by 5 MPa, and at each decrease, the two-way valve 13 is shut off, and the weight of the degreasing cotton 15 is weighed to measure the amount of produced oil. The amount of $CO_2$ flowed back is measured by the measuring cylinder 20. The pressure is successively decreased to the atmospheric pressure. The liquid containing dish 21 serves to receive liquid.

The experimental method of the present disclosure includes the following steps.

At step (1), the dry weight, length, and diameter of a rock core are measured, and the rock core is saturated with a simulated oil. Then the wet weight of the rock core is measured to calculate the amount of the saturated oil.

At step (2), the fully saturated rock core is put into nuclear magnetic resonance equipment to test the distribution of the simulated oil in the rock core.

At step (3), a supercritical $CO_2/H_2O$ huff and puff experiment is carried out.

At i), a supercritical $CO_2/H_2O$ mixed fluid is prepared. The $CO_2$ storage tank is opened, a certain amount of $CO_2$ into the vessel, and the pressure of the vessel is read from the first pressure gauge 5. The amount of $CO_2$ in the vessel is calculated according to the ideal gas law.

The ideal gas law is as follows:

$$PV = nZRT \quad (1)$$

where:
P—pressure of gas, Pa
V—volume of gas, m³
n—amount of substance of gas, mol
Z—compressibility factor of gas;
R—proportionality coefficient, J/(mol·K)
T—system temperature, K Water vapor is introduced into the vessel, and the pressure and relative humidity of the vessel are recorded. According to the molar content and temperature of water vapor in a mixed fluid designed in an experiment scheme, when the ratio of the relative humidity and the pressure meets requirements of the experiment, the water vapor generator 4 is turned off. Then the preparation of a mixed fluid with a certain content of water vapor is completed. The pressure of the vessel is recorded then. Calculation formulas are as follows:

Relative humidity is converted into molar content of water vapor in gas according to the following formulas:

Relative humidity:

$$\frac{e}{E} = \varphi \quad (2)$$

where:
e—actual water vapor pressure in humid air, Pa
E—saturated water vapor pressure at the same temperature, Pa
φ—relative humidity
conversion formula:

$$\varphi = \frac{P \cdot h}{P_0} \quad (3)$$

$$h = \frac{\varphi \cdot P_0}{P} \quad (4)$$

$$\frac{h}{P_0} = \frac{\varphi}{P} \quad (5)$$

where:
φ—relative humidity
P—gas pressure in the vessel, Pa
h—molar content of water vapor in gas
$P_0$—saturated vapor pressure of water at experimental temperature At ii), the mixed gas is pumped into the core holder by the third booster pump 10 while the pressure in the vessel is kept constant by the displacement pump 23. The pressure at the inlet end of the core holder, after reaching an experiment pressure, is kept stable for a certain period of time, and the volume of pumped gas is obtained by the gas flow meter 9.

At iii), the injection valve 11 is shut off so that the entire rock core is in a shut-in state. At the beginning of shut-in, in a stage where supercritical $CO_2/H_2O$ interacts with the rock core, the temperature of the thermostat chamber is adjusted to reach the supercritical state of $H_2O$. After the shut-in has been carried out for a period of time (the change in the overall pressure of the system is recorded during the shut-in), the two-way valve 13 is opened, and the volume of liquid and gas flowed back is measured. The flowback pressure is successively decreased by 5 MPa. At the same time, the volume of carbon dioxide is converted to a volume at the initial pressure of carbon dioxide or the pressure of the mixing vessel 7, and the storage factor of supercritical $CO_2$ is calculated.

The calculation formula for converting the volume of carbon dioxide measured by the measuring cylinder to the volume of the carbon dioxide at the pressure of mixing vessel is based on formula (1).

The compressibility factor of carbon dioxide at the initial pressure may be derived by formula (1):

$$Z_1 = \frac{P_1 V_1}{n_1 R T_1} \quad (6)$$

where:
$P_1$—pressure of carbon dioxide at the pressure of the mixing vessel, Pa
$V_1$—volume of carbon dioxide at the pressure of the mixing vessel, $m^3$
$n_1$—amount of substance of carbon dioxide at the pressure of the mixing vessel, mol
$Z_1$—compressibility factor of carbon dioxide at the pressure of the mixing vessel;
$T_1$—temperature at the pressure of the mixing vessel, K The compressibility factor of carbon dioxide with the equivalent amount of substance at atmospheric pressure is obtained as follows:

$$Z_2 = \frac{P_2 V_2}{n_1 R T_2} \quad (7)$$

where:
$P_2$—atmospheric pressure, Pa
$V_2$—volume of carbon dioxide at atmospheric pressure, $m^3$
$n_1$—amount of substance of carbon dioxide at atmospheric pressure, mol
$Z_2$—compressibility factor of carbon dioxide at atmospheric pressure;
$T_2$—room temperature, K Therefore, the volume of carbon dioxide at atmospheric pressure is converted into a volume at the pressure of the mixing vessel by the following formula:

$$V_1 = \frac{Z_1 P_2 V_2 T_1}{Z_2 P_1 T_2} \quad (8)$$

The storage factor of supercritical $CO_2$ is calculated by the following formula:

$$\eta = \frac{V_{flowback}}{V_{injection}} \quad (9)$$

where:
$\eta$—storage factor of supercritical $CO_2$;
$V_{injection}$—volume of actually injected mixed fluid, $m^3$ (here the injected volume may be obtained directly by the gas flow meter)
$V_{flowback}$—volume at the pressure of the mixing vessel 7 converted from the volume of $CO_2$ flowed back measured by the measuring cylinder, $m^3$.

At step (4), after the experiment is finished, the rock core is put into the nuclear magnetic resonance equipment to test the distribution of the simulated oil in the rock core.

Embodiment 2

In this embodiment, an actual geological shale rock core from an oil field in China was used to assess the effect of supercritical $CO_2/H_2O$ mixed fluid huff and puff in improving the recovery in shale reservoir development. A supercritical $CO_2$ huff and puff experiment and a supercritical $CO_2/H_2O$ experiment were carried out. The experiments included the following steps.

Supercritical $CO_2$ huff and puff experiment:

At step (1), an oil sample was obtained for the experiment: formation oil.

At step (2), the basic physical properties of the rock core were tested: the dry weight, length and diameter of the rock core were measured, and the rock core was saturated with simulated oil. Then the wet weight of the rock core was measured to calculated the amount of the saturated oil.

At step (3), initial distribution of crude oil was determined: the fully saturated rock core was put into nuclear magnetic resonance equipment to test the distribution of the simulated oil in the rock core.

At step (4), a supercritical $CO_2$ huff and puff experiment was carried out: the device of the present disclosure was used, and the vessel and the pipelines were vacuumized by the vacuum pump. The temperature of the thermostat chamber was set to 70° C., the oil-saturated rock core was put into the core holder, and a confining pressure was applied to the core holder by the hand pump, the confining pressure being 25 MPa. The $CO_2$ storage tank was opened, and the first booster pump was turned on to inject a certain amount of gas into the vessel. The pressure of the third booster pump was set to 20 MPa, the injection valve was opened, and $CO_2$ was injected into the core holder. When the inlet pressure reached 20 MPa, the injection was continued with the pressure constant for 1 h, and then the injection valve was shut off. Shut-in operation was carried out, and the inlet pressure was monitored by the second pressure gauge and the outlet pressure by the fourth pressure gauge during the shut-in. The initial weight of the degreasing cotton was weighed before the degreasing cotton was put into the drying pipe. The two-way valve was opened when the shut-in was completed, the pressure was decreased by 5 MPa for each time, and the two-way valve was shut-off at each decrease. The weight of the degreasing cotton was weighed to measure the amount of produced oil. The amount of produced gas was measured by the measuring cylinder. The pressure was successively decreased to the atmospheric pressure.

At step (5), the distribution of crude oil after the experiment was determined: the rock core was put into the nuclear magnetic resonance equipment to test the distribution of the simulated oil in the rock core.

Supercritical $CO_2/H_2O$ mixed fluid huff and puff experiment:

At step (1), the experiment fluid was prepared: the oil sample used in the experiment was formation oil. The vacuum pump was turned on to vacuumize the vessel and the pipelines. The $CO_2$ storage tank was opened, a certain amount of $CO_2$ was injected into the vessel by the first booster pump, and the pressure of the vessel was read from the first pressure gauge. The water vapor generator was turned on, and water vapor was injected into the vessel by the second booster pump. The pressure was read from the first pressure gauge, and the relative humidity is read from the hygronom. When the ratio of the relative humidity and the pressure met requirements of the experiment (in this experiment, it required the molar content of water vapor to be 0.0131 and saturated vapor pressure at 70° C. to be 0.031176 MPa, namely when the ratio of the relative humidity and the pressure was 0.42), the water vapor generator was turned off. Then the pressure of the vessel was recorded. The preparation of a mixed fluid with a water vapor content of 0.0131 in the finished gas was completed.

At step (2), the basic physical properties of the rock core were tested: the dry weight, length and diameter of the rock core were measured, and the rock core was saturated with simulated oil. Then the wet weight of the rock core was measured to calculated the amount of the saturated oil.

At step (3), the initial distribution of crude oil was determined: the fully saturated rock core was put into nuclear magnetic resonance equipment to test the distribution of the simulated oil in the rock core.

At step (4), a supercritical $CO_2/H_2O$ mixed fluid huff and puff experiment was carried out: the temperature of the thermostat chamber was set to 70° C., the saturated rock core was put into the core holder, and a confining pressure was applied to the core holder by the hand pump, the confining pressure being 25 MPa. The pressure of the third booster pump was set to 20 MPa, the injection valve was opened, and the mixed fluid in the vessel was injected into the core holder. When the inlet pressure reached 20 MPa, the injection was continued with the pressure constant for 1 h, and then the injection valve was shut off. Shut-in operation was carried out, and the inlet pressure of the core holder was monitored by the second pressure gauge and the outlet pressure by the fourth pressure gauge during the shut-in. The initial weight of the degreasing cotton was weighed before the degreasing cotton was put into the drying pipe. The two-way valve was opened when the shut-in was completed, the pressure was decreased by 5 MPa for each time, and the two-way valve was shut-off at each decrease. The weight of the degreasing cotton was weighed to measure the amount of produced oil. The amount of $CO_2$ flowed back was measured by the measuring cylinder. The pressure was successively decreased to the atmospheric pressure.

At step (5), the distribution of crude oil after the experiment was determined: the rock core was put into the nuclear magnetic resonance equipment to test the distribution of the simulated oil in the rock core.

Figure 2:
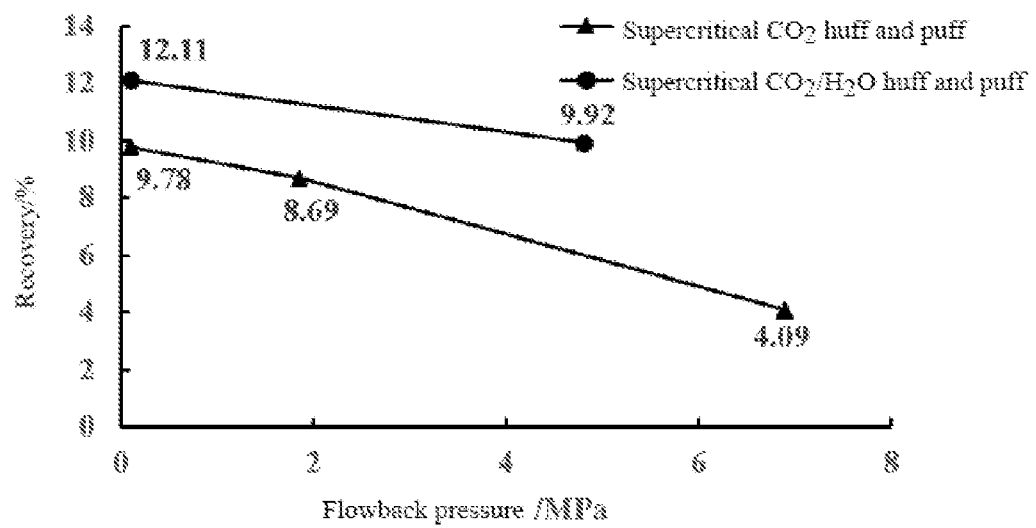
FIG. 2 shows a chart comparing recoveries under different flowback pressures according to an embodiment of the present disclosure.
Figure 3:
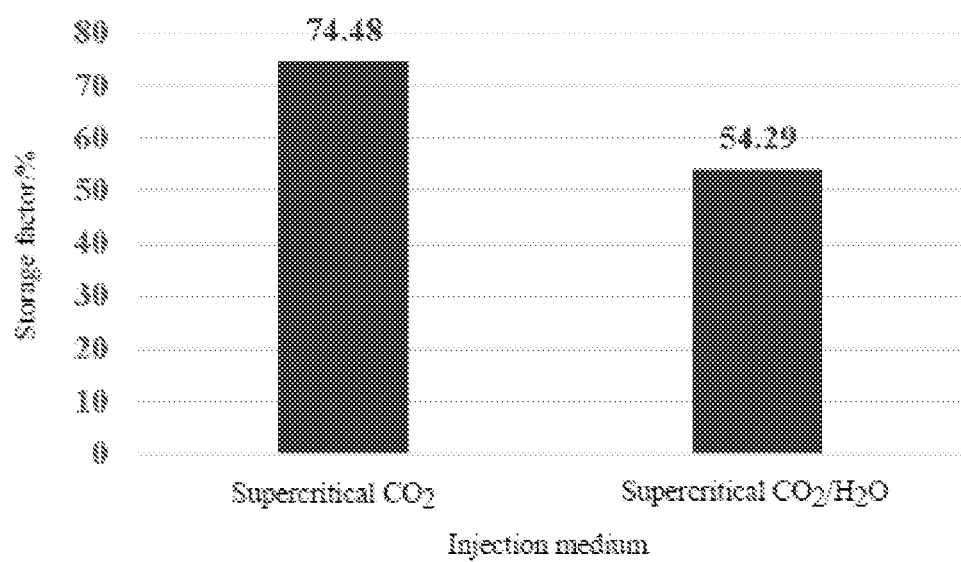
FIG. 3 shows a chart comparing storage factors of supercritical $CO_2$ with different injection media according to an embodiment of the present disclosure.

The recoveries with different flowback pressures of the two experiments are shown in FIG. 2. FIG. 3 shows a chart comparing the storage factors of supercritical $CO_2$. The simultaneous injection of supercritical $CO_2/H_2O$ brought a higher oil recovery but a lower storage factor; and the single injection of supercritical $CO_2$ brought a higher storage factor but lower oil recovery. Due to the presence of $H_2O$, the entry of supercritical $CO_2$ was delayed, and more supercritical $CO_2/H_2O$ was accumulated at the inlet of the rock core. However, when supercritical $CO_2$ was injected alone, continuous gas channels were likely to form inside the rock core extending deeply into the rock core, so that $CO_2$ is difficult to flow back, the storage factor was high, and less crude oil was carried out. The inlet and outlet pressure changes of the two experiments during the shut-in are shown in Table 1. With different injection media, both the inlet pressures of the rock core present a trend of decrease while both the outlet pressures present a trend of increase. Due to the large initial pressure difference of supercritical $CO_2/H_2O$, the outlet pressure has a large increment. When supercritical $CO_2$ was injected alone, the final stable pressure of the rock core was higher, and internal energy was higher. This indicates that the more supercritical $CO_2$ there is, the stronger its dissolution expansion effect.

TABLE 1

| Injection medium | Initial inlet pressure/MPa | Initial outlet pressure/MPa | Final inlet pressure/MPa | Final outlet pressure/MPa | Final stabilized pressure/MPa |
|---|---|---|---|---|---|
| Supercritical $CO_2$ | 20.56 | 7.42 | 12.10 | 9.94 | 11.02 |
| Supercritical $CO_2/H_2O$ | 20.48 | 4.46 | 11.23 | 9.46 | 10.345 |

Figure 4:
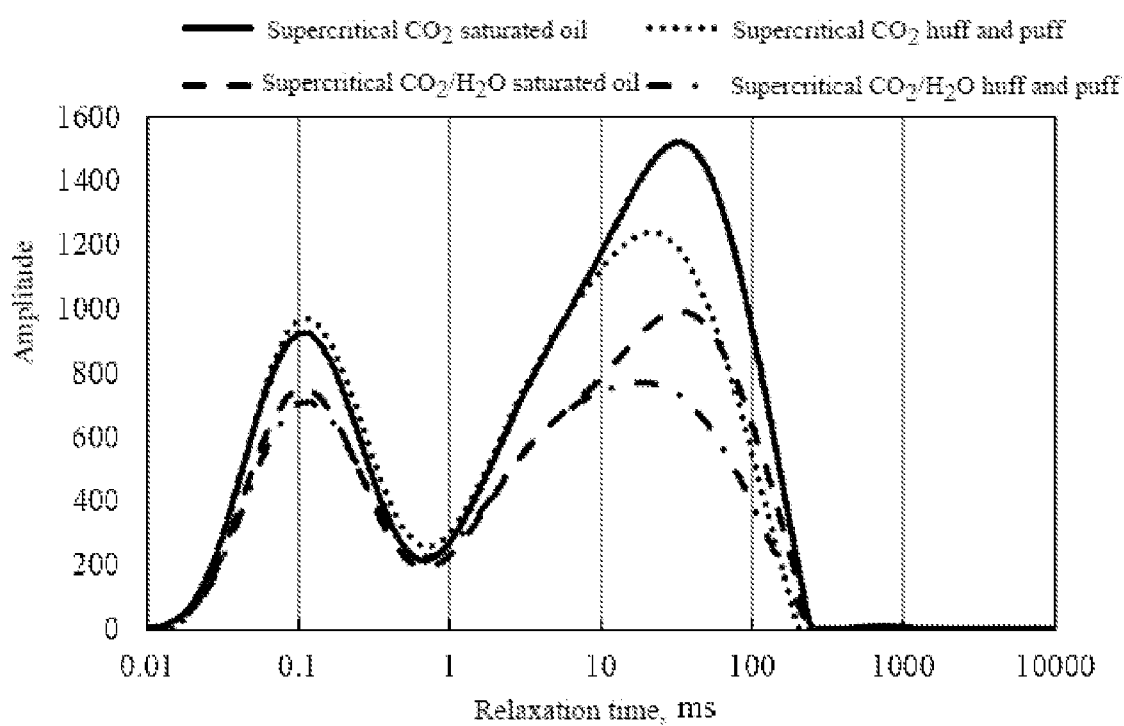
FIG. 4 shows nuclear magnetic resonance $T_2$ spectrums of two experiments.
Figure 5:
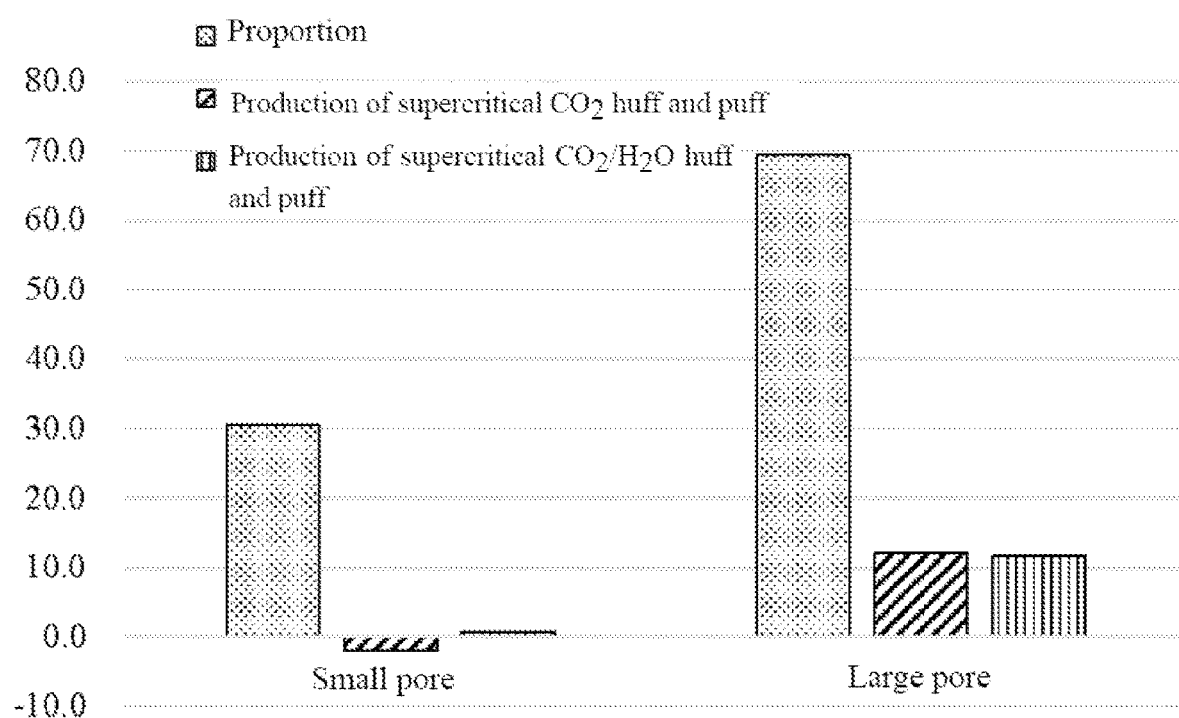
FIG. 5 shows a chart comparing crude oil production of different pore sizes.

FIG. 4 shows nuclear magnetic resonance (NMR) $T_2$ spectrums obtained by the experiments, and FIG. 5 shows the proportions of different pores and the productions under different pore sizes calculated according to NMR data. As the properties of the rock cores are same, the distribution ratios of pores of different sizes are same. When supercritical $CO_2$ was injected alone, crude oil in small pores increased, because supercritical $CO_2$ dissolved in the crude oil expanded the crude oil and pushed the crude oil partly into the small pores. In huff and puff injection of supercritical $CO_2/H_2O$, the viscosity of the injection medium increased, and the crude oil would not be pushed into the small pores. During flowback, supercritical $CO_2/H_2O$ produced more oil from the small pores, which is also the reason for its higher final recovery than single injection of $CO_2$. NMR calculated recoveries and experimentally measured recoveries are shown in Table 2. It can be seen that the experimental device and method of the present disclosure have high measurement accuracy.

TABLE 2

| Injection medium | Recovery by NMR | Recovery by experiment measurement | Relative error |
|---|---|---|---|
| Supercritical $CO_2$ | 10.318% | 9.78% | 5.21% |
| Supercritical $CO_2/H_2O$ | 12.304% | 12.11% | 1.58% |

It can be seen from the above experiment tests that the experimental method and device designed by the present disclosure can be used to accurately assess the effect of supercritical $CO_2/H_2O$ mixed fluid huff and puff on shale oil recovery. In addition to the method set forth in this embodi-

What is claimed is:

1. An experimental method for supercritical $CO_2/H_2O$ mixed fluid huff and puff for shale oil development, using an experimental device for supercritical $CO_2/H_2O$ mixed fluid huff and puff for shale oil development, the experimental device comprising a $CO_2$ storage tank, a water vapor generator, a mixing vessel, and a core holder, wherein the $CO_2$ storage tank is in communication with the mixing vessel via a $CO_2$ delivery pipeline, and the $CO_2$ delivery pipeline is provided with a first booster pump; the water vapor generator is in communication with the mixing vessel via a water vapor delivery pipeline, and the water vapor delivery pipeline is provided with a second booster pump;

a first pressure gauge and a hygronom are connected to an upper end of the mixing vessel, a displacement pump is connected to a lower end of the mixing vessel, and the mixing vessel is connected to a vacuum pump; the mixing vessel is connected to an inlet end of the core holder via a mixed fluid delivery pipeline, and the mixed fluid delivery pipeline is provided with a gas flow meter, a third booster pump, an injection valve and a second pressure gauge in sequence;

the core holder is connected to a hand pump via a confining pressure application pipeline, and the confining pressure application pipeline is provided with a third pressure gauge; the inlet end of the core holder is connected to an inlet end of a drying pipe via an oil-gas extraction pipeline, the oil-gas extraction pipeline is provided with a two-way valve, degreasing cotton is provided inside the drying pipe, an outlet end of the drying pipe is connected to a measuring cylinder via a gas extraction pipeline, and the measuring cylinder is disposed upside down in a liquid containing dish, wherein the liquid containing dish and the measuring cylinder are filled with a saturated sodium carbonate solution; an outlet end of the core holder is provided with a fourth pressure gauge for observing outlet pressure in real time; and the mixing vessel, the first pressure gauge, the hygronom, the gas flow meter, the third booster pump, the injection valve, the second pressure gauge, the two-way valve, the core holder and the fourth pressure gauge are all arranged in a thermostat chamber;

the experimental method comprising the following steps:

at step (1), measuring the dry weight, length, and diameter of a rock core, and saturating the rock core with a simulated oil; and measuring the wet weight of the rock core to calculate the amount of the saturated oil;

at step (2), carrying out a supercritical $CO_2/H_2O$ huff and puff experiment:

at i), preparing a supercritical $CO_2/H_2O$ mixed fluid of a certain ratio in the mixing vessel;

at a., establishing a relation formula by the following steps:

converting relative humidity into molar content of water vapor in gas according to the following formulas:

relative humidity:

$$\frac{e}{E} = \varphi \quad (1)$$

where:

e—actual water vapor pressure in humid air, Pa

E—saturated water vapor pressure at the same temperature, Pa

φ—relative humidity conversion formulas:

$$\varphi = \frac{P \cdot h}{P_0} \quad (2)$$

$$h = \frac{\varphi \cdot P_0}{P} \quad (3)$$

$$\frac{h}{P_0} = \frac{\varphi}{P} \quad (4)$$

where:

φ—relative humidity

P—gas pressure in the vessel, Pa h—molar content of water vapor in gas $P_0$—saturated vapor pressure of water at experimental temperature at b., turning on the thermostat chamber to make the temperature in the thermostat chamber be constant; and turning on the vacuum pump to vacuumize the mixing vessel and the pipelines;

opening the $CO_2$ storage tank, injecting a certain amount of $CO_2$ gas into the mixing vessel via the first booster pump and the $CO_2$ delivery pipeline, and reading the pressure of the mixing vessel from the first pressure gauge; then, turning on the water vapor generator, introducing water vapor into the mixing vessel via the second booster pump and the water vapor delivery pipeline, and recording the pressure and relative humidity of the mixing vessel from the first pressure gauge and the hygronom, respectively;

with the formula (4), according to the molar content and temperature of water vapor in a mixed fluid designed in an experiment scheme, when the ratio of the relative humidity and the pressure meets requirements of experiment, turning off the water vapor generator to complete the preparation of a mixed fluid with a certain content of water vapor; and then recording the pressure of the mixing vessel;

at ii), putting the oil-saturated rock core of step (1) into the core holder, and applying a confining pressure to the core holder by the hand pump, the confining pressure applied being displayed by the third pressure gauge;

opening the injection valve, injecting the prepared mixed fluid with a certain molar fraction of water vapor into the core holder by the third booster pump while keeping the pressure of the mixing vessel constant by the displacement pump, keeping the injection pressure, after reaching an experiment pressure, stable for a certain period of time, and recording the volume of injected gas from the gas flow meter; and at iii), shutting off the injection valve, carrying out shut-in on the core holder, and monitoring the pressure during shut-in in real time by the second pressure gauge and the fourth pressure gauge;

weighing the initial weight of the degreasing cotton before putting the degreasing cotton into the drying pipe, opening the two-way valve when the shut-in is completed for flowback of liquid and gas, then weighing the weight of the degreasing cotton to measure the amount of produced oil, and measuring the amount of $CO_2$ flowed back by the measuring cylinder; and obtaining an oil recovery according to the ratio of the measured amount of produced oil to the amount of saturated oil as the measurement result of the experiment.

2. The experimental method for supercritical $CO_2/H_2O$ mixed fluid huff and puff for shale oil development according to claim 1, characterized by further comprising the following steps:

before the supercritical $CO_2/H_2O$ huff and puff experiment, putting the rock core saturated with the simulated oil into nuclear magnetic resonance equipment to test the distribution of the simulated oil in the rock core; and after the experiment is finished, putting the rock core into the nuclear magnetic resonance equipment to test the distribution of the simulated oil in the rock core.

3. The experimental method for supercritical $CO_2/H_2O$ mixed fluid huff and puff for shale oil development according to claim 1, characterized by further comprising a step of calculating the storage factor of supercritical $CO_2$:

after injecting $CO_2$ into the mixing vessel, reading the pressure of the mixing vessel from the first pressure gauge, and calculating the amount of $CO_2$ in the mixing vessel according to the ideal gas law;

the ideal gas law being as follows:

$$PV = nZRT \qquad (5)$$

where:
P—pressure of gas, Pa
V—volume of gas, m³
n—amount of substance of gas, mol
Z—compressibility factor of gas;
R—proportionality coefficient, J/(mol·K)
T—system temperature, K
converting the volume of $CO_2$ at atmospheric pressure measured by the measuring cylinder to a volume of $CO_2$ at the pressure of the mixing vessel:
firstly, deriving a compressibility factor of carbon dioxide at the pressure of the mixing vessel by the formula (5):

$$Z_1 = \frac{P_1 V_1}{n_1 R T_1} \qquad (6)$$

where:
$P_1$—pressure of carbon dioxide at the pressure of the mixing vessel, Pa
$V_1$—volume of carbon dioxide at the pressure of the mixing vessel, m³
$n_1$—amount of substance of carbon dioxide at the pressure of the mixing vessel, mol
$Z_1$—compressibility factor of carbon dioxide at the pressure of the mixing vessel;
$T_1$—temperature at the pressure of the mixing vessel, K obtaining a compressibility factor of carbon dioxide with the equivalent amount of substance at atmospheric pressure:

$$Z_2 = \frac{P_2 V_2}{n_1 R T_2} \qquad (7)$$

where:
$P_2$—atmospheric pressure, Pa
$V_2$—volume of carbon dioxide at atmospheric pressure, m³
$n_1$—amount of substance of carbon dioxide at atmospheric pressure, mol
$Z_2$—compressibility factor of carbon dioxide at atmospheric pressure;
$T_2$—room temperature, K
converting the volume of carbon dioxide at atmospheric pressure into a volume at the pressure of the mixing vessel by the following formula:

$$V_1 = \frac{Z_1 P_2 V_2 T_1}{Z_2 P_1 T_2} \qquad (8)$$

and calculating the storage factor of supercritical $CO_2$ by the following formula:

$$\eta = \frac{V_{flowback}}{V_{injection}} \qquad (9)$$

where:
η—storage factor of supercritical $CO_2$,
$V_{Injection}$—volume of actually injected mixed fluid, m³
$V_{flowback}$—volume at the pressure of the mixing vessel converted from the volume of $CO_2$ flowed back measured by the measuring cylinder, m³.

4. The experimental method for supercritical $CO_2/H_2O$ mixed fluid huff and puff for shale oil development according to claim 1, characterized in that during the flowback of liquid and gas after the shut-in is finished, the flowback pressure is successively decreased by 5 MPa until the pressure is reduced to the atmospheric pressure.

5. The experimental method for supercritical $CO_2/H_2O$ mixed fluid huff and puff for shale oil development according to claim 1, characterized in that supercritical $CO_2/H_2O$ mixed fluid huff and puff is combined with thermal oil recovery, and the method further comprises the steps:

in a stage where supercritical $CO_2/H_2O$ is injected and interacts with the rock core, adjusting the temperature of the thermostat chamber to reach a critical state of supercritical $H_2O$.

* * * * *